(12) United States Patent
Shimomura et al.

(10) Patent No.: US 6,225,081 B1
(45) Date of Patent: May 1, 2001

(54) PROTEIN, DNA CODING FOR SAME AND METHOD OF PRODUCING THE PROTEIN

(75) Inventors: Takeshi Shimomura; Toshiya Kawaguchi; Naomi Kitamura, all of Kanagawa; Keiji Miyazawa, Tokyo, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 08/685,558

(22) Filed: Jul. 24, 1996

(30) Foreign Application Priority Data

Jul. 24, 1995 (JP) .................................................... 7-187135

(51) Int. Cl.[7] ........................... C12N 15/15; C12N 15/70; C12N 15/85; C07K 14/81
(52) U.S. Cl. ................ 435/69.1; 435/252.3; 435/252.33; 435/254.11; 435/254.3; 435/320.1; 435/325; 530/350; 536/23.1
(58) Field of Search .............................. 435/69.1, 320.1, 435/252.3, 252.33, 254.11, 254.3, 325, 419; 530/23.1

(56) References Cited

U.S. PATENT DOCUMENTS 5,106,833 * 4/1992 Broze et al. ........................ 514/12

FOREIGN PATENT DOCUMENTS

WO 98/25959 * 6/1998 (WO) .

OTHER PUBLICATIONS

Accession W39772 "zc80f02.r1 Pancreatic Islet Homo sapiens cDNA clone" Submitted to the Genbank database by Hillier et al., Apr. 15, 1996.*

Accesion R53486 "zc80f02.r1 Pancreatic Islet Homo sapiens cDNA clone yj70a12.r1 Homo sapiens cDNA clone 154078" Submitted to the Genbank database by Hillier et al., May 18, 1995.*

Accession W37860 "zc13b02.r1 Soares parathyroid tumor NbHPA Homo sapiens cDNA clone 322155 5' similar to SW:IBP_TURRS P00993 Chelonianin" Submitted to the Genbank database by Hillier et al., May 15, 1996.*

Shimomura et al., Hepatocyte growth factor activator inhibitor, a novel Kunitz–type serine protease inhibitor., 1997, J Biol Chem, vol. 272, No. 10, pp. 6370–6376, Mar. 7, 1997.*

Miyazawa et al, *Journal of Biological Chemistry*, 268(14) : 10024–10028 (1993).

Miyazawa et al, *Journal of Biological Chemistry*, 271,(7) : 3615–3618 (1996).

* cited by examiner

*Primary Examiner*—Ponnathapu Achutamurthy
*Assistant Examiner*—William W. Moore
(74) *Attorney, Agent, or Firm*—Sughrue, Mion, Zinn, Macpeak & Seas, PLLC

(57) ABSTRACT

A novel protein having inhibitory activity on the protease activity of hepatocyte growth factor (HGF) activator was purified and isolated, and its molecular weight (ca. 40,000 daltons) and its N-terminal and partial amino acid sequences were determined. A gene coding for the protein was cloned, and the gene DNA was incorporated into a vector, for transforming host cells. Cultivation of the transformant gave the desired protein. The protein can be used as an in vivo or in vitro control factor for HGF or HGF activator. It is also useful as an antigen to be used in producing an antibody to be used as means for kinetic studies of the protein, or as a standard in assay systems therefor.

10 Claims, 2 Drawing Sheets

```
                      SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
         (A) LENGTH: 40 amino acids
         (B) TYPE: amino acid
         (D) TOPOLOGY: linear (ii) MOLECULE TYPE: peptide (v) FRAGMENT TYPE: N-terminal fragment (vi) ORIGINAL SOURCE:
         (A) ORGANISM: Homo sapiens
         (B) STRAIN: MKN45

(x) SEQUENCE DESCRIPTION: SEQ ID NO: 1:

Gly Pro Pro Pro Ala Pro Pro Gly Leu Pro Ala Gly Ala Asp Cys Leu
  1               5                  10                  15

Asn Ser Phe Thr Ala Gly Val Pro Gly Phe Val Leu Asp Thr Xaa Ala
             20                  25                  30

Ser Val Ser Asn Gly Ala Thr Phe
             35                  40

(2) INFORMATION FOR SEQ ID NO: 2:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (v) FRAGMENT TYPE: internal fragment (vi) ORIGINAL SOURCE:
         (A) ORGANISM: Homo sapiens
         (B) STRAIN: MKN45

(x) SEQUENCE DESCRIPTION: SEQ ID NO: 2:

Val Gln Pro Gln Glu Pro Leu Val Leu Lys
  1               5                  10

(2) INFORMATION FOR SEQ ID NO: 3:

(i) SEQUENCE CHARACTERISTICS:
         (A) LENGTH: 21 amino acids
         (B) TYPE: amino acid
         (D) TOPOLOGY: linear (ii) MOLECULE TYPE: peptide
```

(v) FRAGMENT TYPE: internal fragment (vi) ORIGINAL SOURCE:
            (A) ORGANISM: Homo sapiens
            (B) STRAIN: MKN45

(x) SEQUENCE DESCRIPTION: SEQ ID NO: 3:

Asp Val Glu Asn Thr Asp Trp Arg Leu Leu Arg Gly Asp Thr Asp Val
 1               5                  10                  15

Arg Val Glu Arg Lys
            20

(2) INFORMATION FOR SEQ ID NO: 4:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (v) FRAGMENT TYPE: internal fragment (vi) ORIGINAL SOURCE:
            (A) ORGANISM: Homo sapiens
            (B) STRAIN: MKN45

(x) SEQUENCE DESCRIPTION: SEQ ID NO: 4:

Ala Trp Ala Gly Ile Asp Leu Lys
 1               5

(2) INFORMATION FOR SEQ ID NO: 5:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (v) FRAGMENT TYPE: internal fragment (vi) ORIGINAL SOURCE:
            (A) ORGANISM: Homo sapiens
            (B) STRAIN: MKN45

(x) SEQUENCE DESCRIPTION: SEQ ID NO: 5:

Ser Xaa Val Tyr Gly Gly Xaa Leu Gly Asn Lys
 1               5                  10

(2) INFORMATION FOR SEQ ID NO: 6:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (v) FRAGMENT TYPE: internal fragment (vi) ORIGINAL SOURCE:
            (A) ORGANISM: Homo sapiens
            (B) STRAIN: MKN45

(x) SEQUENCE DESCRIPTION: SEQ ID NO: 6:

Asp Pro Asn Gln Val Glu Leu Trp Gly Leu Lys
 1               5                  10

(2) INFORMATION FOR SEQ ID NO: 7:

(i) SEQUENCE CHARACTERISTICS:
            (A) LENGTH: 17 amino acids
            (B) TYPE: amino acid
            (D) TOPOLOGY: linear (ii) MOLECULE TYPE: peptide (v) FRAGMENT TYPE: internal fragment (vi) ORIGINAL SOURCE:
            (A) ORGANISM: Homo sapiens
            (B) STRAIN: MKN45

(x) SEQUENCE DESCRIPTION: SEQ ID NO: 7:

```
Asn Asn Tyr Leu Arg Xaa Xaa Xaa Xaa Ile Leu Ala Xaa Arg Gly Val
 1               5                  10                  15

Gln
```

(2) INFORMATION FOR SEQ ID NO: 8:

(i) SEQUENCE CHARACTERISTICS:
            (A) LENGTH: 1542 base pairs
            (B) TYPE: nucleic acid
            (C) STRANDEDNESS: double
            (D) TOPOLOGY: linear (ii) MOLECULE TYPE: cDNA to mRNA (iv) ANTI-SENSE: no (v) ORIGINAL SOURCE:
            (A) ORGANISM: Homo sapiens
            (B) STRAIN: MKN45

(ix) FEATURE:
            (A) NAME/KEY: coding sequence
            (B) LOCATION: 1 to 1542
            (C) IDENTIFICATION METHOD: by experiment
            (A) NAME/KEY: signal peptide
            (B) LOCATION: 1 to 105
            (C) IDENTIFICATION METHOD: by experiment
            (A) NAME/KEY: mature peptide
            (B) LOCATION: 106 to 1542
            (C) IDENTIFICATION METHOD: by experiment (x) SEQUENCE DESCRIPTION: SEQ ID NO: 8:

```
ATG GCC CCT GCG AGG ACG ATG GCC CGC GCC CGC CTC GCC CCG GCC GGC      48
Met Ala Pro Ala Arg Thr Met Ala Arg Ala Arg Leu Ala Pro Ala Gly
 1               5                  10                  15

ATC CCT GCC GTC GCC TTG TGG CTT CTG TGC ACG CTC GGC CTC CAG GGC      96
Ile Pro Ala Val Ala Leu Trp Leu Leu Cys Thr Leu Gly Leu Gln Gly
                20                  25                  30

ACC CAG GCC GGG CCA CCG CCC GCG CCC CCT GGG CTG CCC GCG GGA GCC     144
Thr Gln Ala Gly Pro Pro Pro Ala Pro Pro Gly Leu Pro Ala Gly Ala
     35                  40                  45

GAC TGC CTG AAC AGC TTT ACC GCC GGG GTG CCT GGC TTC GTG CTG GAC     192
Asp Cys Leu Asn Ser Phe Thr Ala Gly Val Pro Gly Phe Val Leu Asp
 50                  55                  60

ACC AAC GCC TCG GTC AGC AAC GGA GCT ACC TTC CTG GAG TCC CCC ACC     240
Thr Asn Ala Ser Val Ser Asn Gly Ala Thr Phe Leu Glu Ser Pro Thr
 65                  70                  75                  80

GTG CGC CGG GGC TGG GAC TGC GTG CGC GCC TGC TGC ACC ACC CAG AAC     288
Val Arg Arg Gly Trp Asp Cys Val Arg Ala Cys Cys Thr Thr Gln Asn
                 85                  90                  95

TGC AAC TTG GCG CTA GTG GAG CTG CAG CCC GAC CGC GGG GAG GAC GCC     336
Cys Asn Leu Ala Leu Val Glu Leu Gln Pro Asp Arg Gly Glu Asp Ala
                100                 105                 110
```

```
ATC GCC GCC TGC TTC CTC ATC AAC TGC CTC TAC GAG CAG AAC TTC GTG      384
Ile Ala Ala Cys Phe Leu Ile Asn Cys Leu Tyr Glu Gln Asn Phe Val
        115                 120                 125

TGC AAG TTC GCG CCC AGG GAG GGC TTC ATC AAC TAC CTC ACG AGG GAA      432
Cys Lys Phe Ala Pro Arg Glu Gly Phe Ile Asn Tyr Leu Thr Arg Glu
130                 135                 140

GTG TAC CGC TCC TAC CGC CAG CTG CGG ACC CAG GGC TTT GGA GGG TCT      480
Val Tyr Arg Ser Tyr Arg Gln Leu Arg Thr Gln Gly Phe Gly Gly Ser
145                 150                 155                 160

GGG ATC CCC AAG GCC TGG GCA GGC ATA GAC TTG AAG GTA CAA CCC CAG      528
Gly Ile Pro Lys Ala Trp Ala Gly Ile Asp Leu Lys Val Gln Pro Gln
                165                 170                 175

GAA CCC CTG GTG CTG AAG GAT GTG GAA AAC ACA GAT TGG CGC CTA CTG      576
Glu Pro Leu Val Leu Lys Asp Val Glu Asn Thr Asp Trp Arg Leu Leu
                180                 185                 190

CGG GGT GAC ACG GAT GTC AGG GTA GAG AGG AAA GAC CCA AAC CAG GTG      624
Arg Gly Asp Thr Asp Val Arg Val Glu Arg Lys Asp Pro Asn Gln Val
            195                 200                 205

GAA CTG TGG GGA CTC AAG GAA GGC ACC TAC CTG TTC CAG CTG ACA GTG      672
Glu Leu Trp Gly Leu Lys Glu Gly Thr Tyr Leu Phe Gln Leu Thr Val
    210                 215                 220

ACT AGC TCA GAC CAC CCA GAG GAC ACG GCC AAC GTC ACA GTC ACT GTG      720
Thr Ser Ser Asp His Pro Glu Asp Thr Ala Asn Val Thr Val Thr Val
225                 230                 235                 240

CTG TCC ACC AAG CAG ACA GAA GAC TAC TGC CTC GCA TCC AAC AAG GTG      768
Leu Ser Thr Lys Gln Thr Glu Asp Tyr Cys Leu Ala Ser Asn Lys Val
                245                 250                 255

GGT CGC TGC CGG GGC TCT TTC CCA CGC TGG TAC TAT GAC CCC ACG GAG      816
Gly Arg Cys Arg Gly Ser Phe Pro Arg Trp Tyr Tyr Asp Pro Thr Glu
                260                 265                 270

CAG ATC TGC AAG AGT TTC GTT TAT GGA GGC TGC TTG GGC AAC AAG AAC      864
Gln Ile Cys Lys Ser Phe Val Tyr Gly Gly Cys Leu Gly Asn Lys Asn
            275                 280                 285

AAC TAC CTT CGG GAA GAA GAG TGC ATT CTA GCC TGT CGG GGT GTG CAA      912
Asn Tyr Leu Arg Glu Glu Glu Cys Ile Leu Ala Cys Arg Gly Val Gln
    290                 295                 300

GGC CCC TCC ATG GAA AGG CGC CAT CCA GTG TGC TCT GGC ACC TGT CAG      960
Gly Pro Ser Met Glu Arg Arg His Pro Val Cys Ser Gly Thr Cys Gln
305                 310                 315                 320

CCC ACC CAG TTC CGC TGC AGC AAT GGC TGC TGC ATC GAC AGT TTC CTG     1008
Pro Thr Gln Phe Arg Cys Ser Asn Gly Cys Cys Ile Asp Ser Phe Leu
                325                 330                 335

GAG TGT GAC GAC ACC CCC AAC TGC CCC GAC GCC TCC GAC GAG GCT GCC     1056
Glu Cys Asp Asp Thr Pro Asn Cys Pro Asp Ala Ser Asp Glu Ala Ala
                340                 345                 350

TGT GAA AAA TAC ACG AGT GGC TTT GAC GAG CTC CAG CGC ATC CAT TTC     1104
Cys Glu Lys Tyr Thr Ser Gly Phe Asp Glu Leu Gln Arg Ile His Phe
            355                 360                 365

CCC AGT GAC AAA GGG CAC TGC GTG GAC CTG CCA GAC ACA GGA CTC TGC     1152
Pro Ser Asp Lys Gly His Cys Val Asp Leu Pro Asp Thr Gly Leu Cys
    370                 375                 380

AAG GAG AGC ATC CCG CGC TGG TAC TAC AAC CCC TTC AGC GAA CAC TGC     1200
Lys Glu Ser Ile Pro Arg Trp Tyr Tyr Asn Pro Phe Ser Glu His Cys
385                 390                 395                 400

GCC CGC TTT ACC TAT GGT GGT TGT TAT GGC AAC AAG AAC AAC TTT GAG     1248
Ala Arg Phe Thr Tyr Gly Gly Cys Tyr Gly Asn Lys Asn Asn Phe Glu
                405                 410                 415

GAA GAG CAG CAG TGC CTC GAG TCT TGT CGC GGC ATC TCC AAG AAG GAT     1296
Glu Glu Gln Gln Cys Leu Glu Ser Cys Arg Gly Ile Ser Lys Lys Asp
            420                 425                 430
```

```
GTG TTT GGC CTG AGG CGG GAA ATC CCC ATT CCC AGC ACA GGC TCT GTG    1344
Val Phe Gly Leu Arg Arg Glu Ile Pro Ile Pro Ser Thr Gly Ser Val
        435                 440                 445

GAG ATG GCT GTC GCA GTG TTC CTG GTC ATC TGC ATT GTG GTG GTG GTA    1392
Glu Met Ala Val Ala Val Phe Leu Val Ile Cys Ile Val Val Val Val
        450                 455                 460

GCC ATC TTG GGT TAC TGC TTC TTC AAG AAC CAG AGA AAG GAC TTC CAC    1440
Ala Ile Leu Gly Tyr Cys Phe Phe Lys Asn Gln Arg Lys Asp Phe His
465                 470                 475                 480

GGA CAC CAC CAC CAC CCA CCA CCC ACC CCT GCC AGC TCC ACT GTC TCC    1488
Gly His His His His Pro Pro Pro Thr Pro Ala Ser Ser Thr Val Ser
                485                 490                 495

ACT ACC GAG GAC ACG GAG CAC CTG GTC TAT AAC CAC ACC ACC CGG CCC    1536
Thr Thr Glu Asp Thr Glu His Leu Val Tyr Asn His Thr Thr Arg Pro
            500                 505                 510

CTC TGA                                                             1542
Leu *
```

(2) INFORMATION FOR SEQ ID NO: 9:

(i) SEQUENCE CHARACTERISTICS:
        (A) LENGTH: 17 nucleotides
        (B) TYPE: nucleic acid
        (C) STRANDEDNESS: single stranded
        (D) TOPOLOGY: linear (ii) MOLECULE TYPE: other nucleic acid, synthetic DNA (x) SEQUENCE DESCRIPTION: SEQ ID NO: 9:

```
GGNGCNGAYT GYTTRAA                                                    17
```

(2) INFORMATION FOR SEQ ID NO: 10:

(i) SEQUENCE CHARACTERISTICS:
        (A) LENGTH: 17 nucleotides
        (B) TYPE: nucleic acid
        (C) STRANDEDNESS: single stranded
        (D) TOPOLOGY: linear (ii) MOLECULE TYPE: other nucleic acid, synthetic DNA (x) SEQUENCE DESCRIPTION: SEQ ID NO: 10:

```
GGNGCNGAYT GYCNRAA                                                    17
```

(2) INFORMATION FOR SEQ ID NO: 11:

(i) SEQUENCE CHARACTERISTICS:
        (A) LENGTH: 17 nucleotides
        (B) TYPE: nucleic acid
        (C) STRANDEDNESS: single stranded
        (D) TOPOLOGY: linear (ii) MOLECULE TYPE: other nucleic acid, synthetic DNA (x) SEQUENCE DESCRIPTION: SEQ ID NO: 11:

```
GTRTCYAANA CRAANCC                                                    17
```

(2) INFORMATION FOR SEQ ID NO: 12:

(i) SEQUENCE CHARACTERISTICS:
        (A) LENGTH: 17 nucleotides
        (B) TYPE: nucleic acid
        (C) STRANDEDNESS: single stranded
        (D) TOPOLOGY: linear (ii) MOLECULE TYPE: other nucleic acid, synthetic DNA (x) SEQUENCE DESCRIPTION: SEQ ID NO: 12:

GTRTCNAGNA CRAANCC                                                17

(2) INFORMATION FOR SEQ ID NO: 13:

(i) SEQUENCE CHARACTERISTICS:
           (A) LENGTH: 17 nucleotides
           (B) TYPE: nucleic acid
           (C) STRANDEDNESS: single stranded
           (D) TOPOLOGY: linear (ii) MOLECULE TYPE: other nucleic acid, synthetic DNA (x) SEQUENCE DESCRIPTION: SEQ ID NO: 13:

CCNCCRTANA CRAANGA                                                17

(2) INFORMATION FOR SEQ ID NO: 14:

(i) SEQUENCE CHARACTERISTICS:
           (A) LENGTH: 17 nucleotides
           (B) TYPE: nucleic acid
           (C) STRANDEDNESS: single stranded
           (D) TOPOLOGY: linear (ii) MOLECULE TYPE: other nucleic acid, synthetic DNA (x) SEQUENCE DESCRIPTION: SEQ ID NO: 14:

CCNCCRTANA CRAARCT                                                17

(2) INFORMATION FOR SEQ ID NO: 15:

(i) SEQUENCE CHARACTERISTICS:
           (A) LENGTH: 17 nucleotides
           (B) TYPE: nucleic acid
           (C) STRANDEDNESS: single stranded
           (D) TOPOLOGY: linear (ii) MOLECULE TYPE: other nucleic acid, synthetic DNA (x) SEQUENCE DESCRIPTION: SEQ ID NO: 15:

CCCCANAGYT CNACYTG                                                17

(2) INFORMATION FOR SEQ ID NO: 16:

(i) SEQUENCE CHARACTERISTICS:
           (A) LENGTH: 13 nucleotides
           (B) TYPE: nucleic acid
           (C) STRANDEDNESS: single stranded
           (D) TOPOLOGY: linear (ii) MOLECULE TYPE: other nucleic acid, synthetic DNA (x) SEQUENCE DESCRIPTION: SEQ ID NO: 16:

AACAGCTTTA CCG                                                    13

(2) INFORMATION FOR SEQ ID NO: 17:

(i) SEQUENCE CHARACTERISTICS:
           (A) LENGTH: 17 nucleotides
           (B) TYPE: nucleic acid
           (C) STRANDEDNESS: single
           (D) TOPOLOGY: linear (ii) MOLECULE TYPE: other nucleic acid, synthetic DNA (x) SEQUENCE DESCRIPTION: SEQ ID NO: 17:

CCCCAYAAYT CNACYTG                                                17

(2) INFORMATION FOR SEQ ID NO: 18:

(i) SEQUENCE CHARACTERISTICS:
        (A) LENGTH: 513 amino acids
        (B) TYPE: amino acid
        (C) STRANDEDNESS: single
        (D) TOPOLOGY: linear (ii) MOLECULE TYPE: peptide (v) ORIGINAL SOURCE:
        (A) ORGANISM: Homo sapiens
        (B) STRAIN: MKN45

(x) SEQUENCE DESCRIPTION: SEQ ID NO: 18:

```
Met Ala Pro Ala Arg Thr Met Ala Arg Ala Arg Leu Ala Pro Ala Gly
 1               5                  10                  15

Ile Pro Ala Val Ala Leu Trp Leu Leu Cys Thr Leu Gly Leu Gln Gly
                20                  25                  30

Thr Gln Ala Gly Pro Pro Ala Pro Pro Gly Leu Pro Ala Gly Ala
            35                  40                  45

Asp Cys Leu Asn Ser Phe Thr Ala Gly Val Pro Gly Phe Val Leu Asp
        50                  55                  60

Thr Asn Ala Ser Val Ser Asn Gly Ala Thr Phe Leu Glu Ser Pro Thr
 65                  70                  75                  80

Val Arg Arg Gly Trp Asp Cys Val Arg Ala Cys Cys Thr Thr Gln Asn
                85                  90                  95

Cys Asn Leu Ala Leu Val Glu Leu Gln Pro Asp Arg Gly Glu Asp Ala
               100                 105                 110

Ile Ala Ala Cys Phe Leu Ile Asn Cys Leu Tyr Glu Gln Asn Phe Val
               115                 120                 125

Cys Lys Phe Ala Pro Arg Glu Gly Phe Ile Asn Tyr Leu Thr Arg Glu
           130                 135                 140

Val Tyr Arg Ser Tyr Arg Gln Leu Arg Thr Gln Gly Phe Gly Gly Ser
145                 150                 155                 160

Gly Ile Pro Lys Ala Trp Ala Gly Ile Asp Leu Lys Val Gln Pro Gln
               165                 170                 175

Glu Pro Leu Val Leu Lys Asp Val Glu Asn Thr Asp Trp Arg Leu Leu
           180                 185                 190

Arg Gly Asp Thr Asp Val Arg Val Glu Arg Lys Asp Pro Asn Gln Val
       195                 200                 205

Glu Leu Trp Gly Leu Lys Glu Gly Thr Tyr Leu Phe Gln Leu Thr Val
   210                 215                 220

Thr Ser Ser Asp His Pro Glu Asp Thr Ala Asn Val Thr Val Thr Val
225                 230                 235                 240

Leu Ser Thr Lys Gln Thr Glu Asp Tyr Cys Leu Ala Ser Asn Lys Val
               245                 250                 255

Gly Arg Cys Arg Gly Ser Phe Pro Arg Trp Tyr Tyr Asp Pro Thr Glu
           260                 265                 270

Gln Ile Cys Lys Ser Phe Val Tyr Gly Gly Cys Leu Gly Asn Lys Asn
       275                 280                 285

Asn Tyr Leu Arg Glu Glu Glu Cys Ile Leu Ala Cys Arg Gly Val Gln
   290                 295                 300

Gly Pro Ser Met Glu Arg Arg His Pro Val Cys Ser Gly Thr Cys Gln
305                 310                 315                 320

Pro Thr Gln Phe Arg Cys Ser Asn Gly Cys Cys Ile Asp Ser Phe Leu
```

-continued

```
                    325                 330                 335
Glu Cys Asp Asp Thr Pro Asn Cys Pro Asp Ala Ser Asp Glu Ala Ala
            340                 345                 350
Cys Glu Lys Tyr Thr Ser Gly Phe Asp Glu Leu Gln Arg Ile His Phe
        355                 360                 365
Pro Ser Asp Lys Gly His Cys Val Asp Leu Pro Asp Thr Gly Leu Cys
    370                 375                 380
Lys Glu Ser Ile Pro Arg Trp Tyr Tyr Asn Pro Phe Ser Glu His Cys
385                 390                 395                 400
Ala Arg Phe Thr Tyr Gly Gly Cys Tyr Gly Asn Lys Asn Asn Phe Glu
                405                 410                 415
Glu Glu Gln Gln Cys Leu Glu Ser Cys Arg Gly Ile Ser Lys Lys Asp
            420                 425                 430
Val Phe Gly Leu Arg Arg Glu Ile Pro Ile Pro Ser Thr Gly Ser Val
        435                 440                 445
Glu Met Ala Val Ala Val Phe Leu Val Ile Cys Ile Val Val Val Val
    450                 455                 460
Ala Ile Leu Gly Tyr Cys Phe Phe Lys Asn Gln Arg Lys Asp Phe His
465                 470                 475                 480
Gly His His His Pro Pro Pro Thr Pro Ala Ser Ser Thr Val Ser
                485                 490                 495
Thr Thr Glu Asp Thr Glu His Leu Val Tyr Asn His Thr Thr Arg Pro
                500                 505                 510
Leu
```

PROTEIN, DNA CODING FOR SAME AND METHOD OF PRODUCING THE PROTEIN

FIELD OF THE INVENTION

The present invention relates to a novel protein and a DNA coding for the same. More particularly, it relates to a novel protein having inhibitory activity on the protease activity of hepatocyte growth factor activating factor (HGF activator) (hereinafter this protein is sometimes referred to also as "HAI-I"), a gene coding for the protein, an expression vector containing the gene, a transformant as transformed with the expression vector, and a method of producing HAI-I using the transformant.

BACKGROUND OF THE INVENTION

It is already reported that thrombin activates the precursor of HGF activator (JP-A-5-103670, JP-A-6-141859, JP-A-6-153946 and JP-A-6-153966 (the term "JP-A" as used herein means an "unexamined published Japanese patent application"); factor having activity to convert the single chain form of hepatocyte growth factor (HGF) to its double chain form) in the manner of positive activity control. However, human tissues-derived protease inhibitor capable of inhibiting, as a negative control factor, the physiological activity of HGF activator has not been known. Therefore, how HGF activator is controlled in human tissues remains unknown. Such a negative control factor might also influence indirectly on the activity of hepatocyte growth factor (HGF) on which HGF activator acts. Thus, for the analysis of the mechanism of action of HGF in vivo, as well, it has been demanded that such a human tissues-derived protease inhibitor be isolated and identified.

By using such a protease inhibitor and an antibody to the protease inhibitor, it would become possible to know the in vivo physiological activity of HGF activator, analyze the mechanism of action thereof or analyze the mechanism of control of HGF activation, from a standpoint different from those of the prior art.

Furthermore, for investigating the detailed in vivo function of HAI-I or the effect of HAI-I in hepatic disorder, for instance, HAI-I is required in large quantities. At present, however, there is only one method available for preparing HAI-I, which method comprises using, as a starting material, the culture supernatant obtained with a human cancer cell line such as MKN45 or A549 cells and purifying therefrom HAI-I occurring therein in trace amounts. This method is not always the best one from the labor, time and cost viewpoint. It encounters great difficulties in stably isolating the minor amount of HAI-I alone. Therefore, it has been desired that an expression system be constructed so that HAI-I can be obtained stably and in large quantities.

SUMMARY OF THE INVENTION

The present inventors have conducted screening of various cultured cell lines using, as an indicator, the inhibitory activity on the protease activity of hepatocyte growth factor activator and have found that a substance having the activity occurs in the culture supernatant of certain human cancer cell lines (MKN45 cells, A549 cells and like epithelial tumor cell lines). To reveal the nature of its inhibitory activity, they further attempted to purify the substance from the MKN45 cell culture supernatant using various column chromatography techniques. As a result, they have found a novel protein with a molecular weight of about 40,000 daltons as determined by SDS (sodium dodecyl sulfate)-polyacrylamide gel electrophoresis (PAGE) and they also have obtained an amino-terminal amino acid sequence of this protein by analyzing the protein on a protein sequencer. Further, they determined partial amino acid sequences by decomposing the protein using proteolytic enzymes, isolating the resultant peptides and subjecting each peptide to the same amino acid sequence analysis as mentioned above. Furthermore, they estimated DNA base sequences based on the partial amino acid sequences and conducted screening of a cDNA library using oligonucleotide probes prepared based on the sequences. As a result, they have succeeded in cloning a gene coding for the protein and have now completed the present invention.

Furthermore, as a result of various investigations to produce the protein stably and in large quantities using the recombinant DNA technique and, the present inventors have constructed a novel expression vector coding for the protein and have enabled expression of the protein. Thus, by constructing a plasmid for protein expression by inserting a DNA fragment coding for part or the whole of the amino acid sequence of the protein into a plasmid vector such as the expression vector pME18S for use in animal cells or an expression vector for use in yeasts, Escherichia coli and the like, at a site downstream from the promoter thereof and using the thus-obtained recombinant plasmid to transform host cells, they have now completed the present invention in another aspect.

The present invention thus relates to a protein having the following physico-chemical properties:

(1) a molecular weight of about 40,000 daltons as determined by SDS-polyacrylamide gel electrophoresis;

(2) inhibitory activity on the protease activity of hepatocyte growth factor activator; and (3) one of the amino acid sequences depicted in the sequence listing under SEQ ID NO:1 through 7 or an amino acid sequence substantially equivalent thereto; proteins respectively having the amino acid sequences depicted in the sequence listing under SEQ ID NO:1 through 7 or amino acid sequences substantially equivalent thereto and having inhibitory activity on the protease activity of hepatocyte growth factor activator; a protein having the amino acid sequence depicted in the sequence listing under SEQ ID NO:18 or an amino acid sequence substantially equivalent thereto; and a protein having, as its amino acid sequence, that segment of the amino acid sequence depicted in the sequence listing under SEQ ID NO:18 which starts with the 36th amino acid (glycine) residue and ends with the 513th amino acid (leucine) residue, or an amino acid sequence substantially equivalent thereto; DNAs and genes coding for the proteins defined above; expression vectors respectively containing the DNA or genes; transformants obtained by transformation of host cells with the expression vectors; as well as a method of producing proteins having inhibitory activity on the protease activity of hepatocyte growth factor activator which comprises cultivating the transformants.

The base sequence shown in the sequence listing under SEQ ID NO:8 contains only one strand, with the other complementary base sequence being omitted. Starting with this gene and using the recombinant DNA technology, it is possible to cause expression of, for example, the protein having the amino acid sequence shown in the sequence listing under SEQ ID NO:18. On that occasion, the protein translated from MRNA coding for the protein contains a signal sequence. After extracellular excretion, however, the signal sequence has been cleaved off and the protein obtained has an amino acid sequence comprising the 36th amino acid (glycine) residue and the subsequent amino acid residues of the amino acid sequence shown in the sequence listing under SEQ ID NO:18. Signal sequences of other proteins may also be used as the signal sequence. For signal sequence-free mature protein expression in host cells, a gene having that portion of the base sequence shown in the sequence listing under SEQ ID NO:8 which comprises the 106th nucleotide (guanine) residue and the subsequent nucleotide residues may be used as the gene coding for the relevant protein and joined to the ATG codon of a vector. The present invention further includes, within the scope thereof, modifications of the proteins or DNAs mentioned above as derived therefrom by deletion, substitution and/or addition of one or more amino acid or nucleotide residues within limits not harmful to the inhibitory activity on the protease activity of HGF activator, namely those proteins or DNAs that respectively have "substantially equivalent amino acid sequences" or "substantially equivalent base sequences".

DETAILED DESCRIPTION OF THE INVENTION

Figure 1:
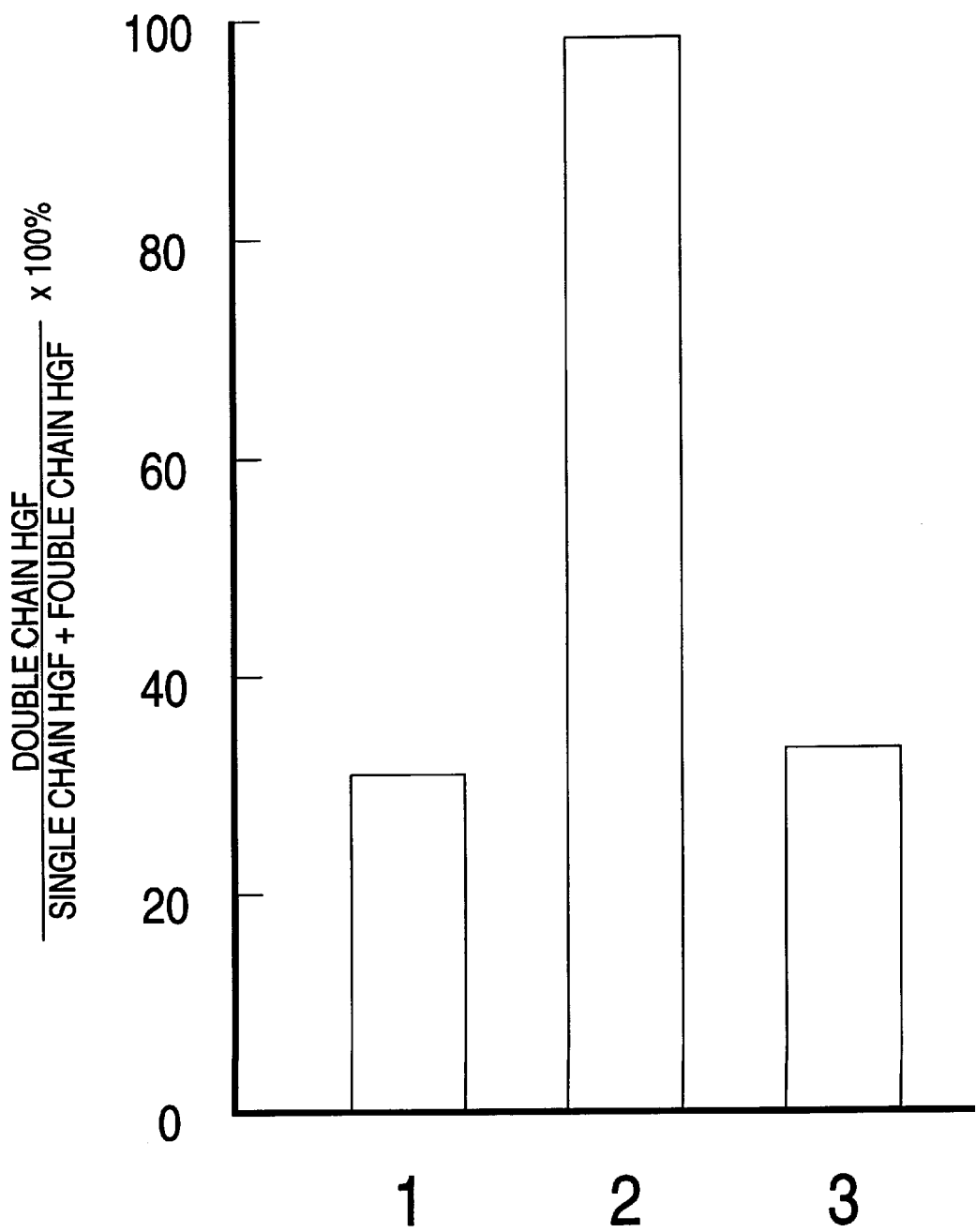
FIG. 1 shows the results of assaying of the protein of the present application for its inhibitory activity on the protease activity of HGF activator.

In the following, the present invention is described in further detail. The novel protein of the present invention which has protease inhibitor activity can be obtained by proceeding via such purification steps as mentioned below. For example, a human cancer cell line (MKN45 cells or A549 cells, deposited with the Japanese Cancer Research Resources Bank under the deposit numbers JCRB0254 and JCRB0076, respectively, or like epithelial tumor cell line) is cultivated in a serum-free medium for several days, the culture supernatant is recovered and, after removal of cells therefrom and concentration, submitted to a heparin-Sepharose column (available e.g. from Pharmacia). The non-adsorbed fraction is submitted to a ConA-Sepharose column (available-e.g. from Pharmacia) and separated into an adsorbed fraction and an non-adsorbed fraction. The adsorbed fraction is subjected to hydrophobic chromatography using Phenyl-5PW (available e.g. from Tosoh Corp.). The thus-obtained fraction containing the desired protein is chromatographed on a DEAE ion exchange column (available e.g. from Polymer Laboratory), then submitted to a hydroxyapatite column (available e.g. from Mitsui Toatsu Chemicals or Seikagaku Corp.), and further to gel filtration column chromatography (using e.g. Asahi Chemical Industry's GS520) to give the protein in question. The purification steps may further include reversed phase column chromatography and/or other appropriate means, as necessary.

Upon SDS-polyacrylamide gel electrophoresis, the thus-purified protein of the present invention migrates as a smear band or several fragments presumably resulting from differences in sugar chain, amino acid residue modification and/or C-terminal side mutation and having a molecular weight of about 40,000 daltons. When reacted with HGF activator, the protein shows inhibitory activity on the protease activity of HGF activator. This protein of the present invention contains the amino acid sequence shown in Table 1 below.

A DNA fragment of the gene coding for the novel protein of the present invention can be obtained in the following manner. By analyzing the novel protein purified in the above manner using a gaseous phase protein sequencer (available e.g. from Applied Biosystems), its amino-terminal amino acid sequence can be determined. Further, the protein is decomposed using lysyl endopeptidase (e.g. Achromobacter protease I), the resulting peptide fragments are separated by reversed phase high-performance liquid chromatography (using e.g. a YMC's column) and each fragment is subjected to amino acid sequence analysis in the same manner as mentioned above, whereby the amino acid sequence of an intermediate portion of the protein can be revealed.

A DNA base sequence is deduced from the amino acid sequence thus determined and, correspondingly, appropriate oligonucleotides are synthesized and used as probes. Human-derived liver, spleen and placenta cDNA libraries (available e.g. from Clonetec), among others, can be used as the cDNA library for screening out the gene coding for the desired protein. In addition, a cDNA library may be constructed in the conventional manner from a cell line or tissue material in which the protein is expressed.

*Escherichia coli* is transfected with λ phage containing such cDNA incorporated therein (the method of Maniatis et al.: "Molecular Cloning") and then cultivated. The plaques formed are subjected to selection by plaque hybridization using oligonucleotide probes prepared based on the base sequence deduced from the amino acid sequence of a portion of the protein in question, whereby a certain number of different λ phage clones having the amino acid sequence of the desired protein and containing, in addition, those segment base sequences of the protein that correspond to other regions than the probes can be obtained with ease.

Then, the phage from each positive plaque obtained in the above screening is then allowed to replicate by the method of Maniatis et al., and DNA is purified therefrom by the glycerol gradient method and, after appropriate restriction enzyme cleavage, submitted to cDNA subcloning into a plasmid vector such as pUC18 or pUC19 or a single chain phage vector such as M13mp18 or M13mp19. Thereafter, the base sequence of the desired cDNA fragment can be determined by the method of Sanger et al. The base sequences of the clones obtained are analyzed and synthesized and, as a result, a gene totally corresponding to the whole amino acid sequence of the desired protein as shown in the sequence listing under SEQ ID NO:18 can be derived from a group of cDNAs coding for respective portions of the protein. It is also possible to obtain a gene containing the whole of the cDNA in question, a gene containing the cDNA with deletion of a partial base sequence thereof, a gene containing the cDNA with insertion of some other base sequence, a gene containing the cDNA with substitution of some other base sequence for a partial base sequence of the cDNA, or the like gene from a variety of cDNA libraries by the PCR method using portions of the cDNA in question as probes. Such site-specific mutation, inclusive of base sequence deletion, addition or substitution, can be readily realized by the methods described in the literature (e.g. Methods in Enzymol., 217, 218 (1993); ibid., 217, 270 (1993)).

The group of cDNAs obtained in the above manner are joined together so that the order of the base sequences is fit to the amino acid sequence of the protein, to give a DNA fragment covering the whole region of the protein. The DNA fragment is inserted into a plasmid, such as pCDL-SRα296, at a site downstream from the promoter thereof and matched in phase with the translation initiation codon ATG, to thereby construct a protein expression vector. Then, the protein can be expressed in a host, for example animal cells, transformed with the plasmid. Thereafter, the protein expressed can be recovered by purification by a conventional method.

Thus, each of the thus-obtained cDNAs is inserted into a plasmid, such as pME18S, at a site downstream from the promoter thereof to thereby construct a plasmid for protein expression. The protein or a protein derived therefrom by partial amino acid sequence deletion, insertion or substitution can be expressed in a host, such as animal cells, transformed with the expression plasmid. More concretely, CHO cells, COS cells, mouse L cells, mouse C127 cells, mouse FM3A cells and the like can be used as the animal cells for protein expression. When these animal cells are used as the host, the use, as a signal sequence, of that portion of the DNA base sequence shown in the sequence listing under SEQ ID NO:8, namely the gene for the protein, which starts with the 1st nucleotide and ends with the 35th nucleotide, or the use of an existing signal sequence is expected to be conducive to extracellular secretory production of the protein or production thereof on the cell membrane.

The expression plasmid for use in animal cell hosts is constructed in the following manner. As the promoter, use can be made of any of the existing promoters, for example the SRα promoter, SV40 promoter or metallothionein gene promoter. A DNA containing the whole gene for the protein, inclusive of the above-mentioned signal-like sequence, a DNA containing the gene with a partial base sequence deletion, a DNA containing the gene with insertion of a base sequence or a DNA containing the gene with substitution of some other sequence for a partial base sequence thereof is inserted into a site downstream from the promoter in the direction of transcription. In constructing the expression plasmid for the protein, two or three pieces of the DNA fragment of the gene coding for the protein may be joined together and used for insertion downstream from the promoter. It is also possible to join such a promoter as the SV40 promoter to the 5' upstream side of the DNA fragment of the gene coding for the protein to give a unit insert and insert, into a vector, two or three such units joined together in the same direction of transcription. A polyadenylation site is added to the downstream side of the gene coding for the protein. For example, the polyadenylation site derived from the SV40 DNA, β-globin gene or metallothionein gene can be joined to the downstream side of the gene coding for the protein. When a DNA fragment comprising a promoter and the gene coding for the protein as joined together is duplicated or triplicated, each unit may contain a polyadenylation site on the 3' side of the gene coding for the protein. In transforming animal cells, for example CHO cells, with such expression vector, a drug resistance gene can be used for the purpose of expression cell selection. As the drug resistance gene, there may be mentioned the DHFR gene which provides resistance to methotrexate (J. Mol. Biol., 159, 601 (1982)), the Neo gene which provides resistance to the antibiotic G-418 (J. Mol. Appl. Genet., 1, 327 (1982)), the Escherichia coli-derived Ecogpt gene which provides resistance to mycophenolic acid (Proc. Natl. Acad. Sci. U.S.A., 78, 2072 (1981)) and the hph gene which provides resistance to the antibiotic hygromycin (Mol. Cell. Biol., 5, 410 (1985)), among others. Each resistance gene contains a promoter, such as the above-mentioned SV40-derived promoter, inserted on the 5' upstream side and a polyadenylation site as mentioned above on the 3' downstream side of each resistance gene. In inserting such resistance gene into the expression vector for the protein, the gene may be inserted at a site downstream from the polyadenylation site of the gene coding for the protein, in either direction, the same or opposite. These expression vectors make it unnecessary to perform double transformation with another plasmid containing a selective marker gene for the purpose of transformant isolation. When the expression vector for the protein does not contain such a selective marker gene insert, a vector having a marker suited for transformant selection, for example pSV2neo (J. Mol. Appl. Genet., 1, 327 (1982)), pMBG (Nature, 294, 228 (1981)), pSV2gpt (Proc. Natl. Acad. Sci. U.S.A., 78, 2072 (1981)) or pAd•D26•1 (J. Mol. Biol., 159, 601 (1982)), may be used, in combination with the expression vector for the gene coding for the protein, for transformation to thereby make it easy to perform transformant selection based on phenotypic expression of the drug resistance gene.

The expression vector can be introduced into animal cells by the calcium phosphate method (Virology, 52, 456 (1973)) or the electroporation method (J. Membr. Biol., 10, 279 (1972)), for instance. The transformed animal cells can be cultivated in the conventional manner in the manner of suspension culture or adhesion culture. They are cultivated in a medium such as MEM or RPMI 1640 in the presence of 5 to 10% of serum or in the presence of an appropriate amount of insulin, transferrin or the like, or under serum-free conditions. Further, it is also possible to produce the protein using microorganisms such as yeasts or *Escherichia coli*, for example strains of *Saccharomyces cerevisiae* or the strain *Escherichia coli* YA-21. Since the cells express the protein in the culture supernatant or on the cell surface, it is possible to recover and purify the protein using the culture supernatant or cells of this transformant. More specifically, the protein can be isolated and purified by subjecting the culture supernatant or cell extract containing the protein produced to an appropriate chromatography procedure, for example chromatographic treatment using heparin-Sepharose, ConA-Sepharose, hydroxyapatite and the like in combination.

The protease inhibitor activity-endowed protein of the present invention has inhibitory activity on the protease activity of HGF activator and, therefore, is useful as a in vitro or in vivo regulatory factor for HGF activator or, indirectly, as a HGF activity regulating factor. The protein as well as an antibody to the protein or a gene coding for the protein is further useful as a tool or means for function analysis of the factors.

Furthermore, by introducing an expression vector carrying a gene coding for the protein into animal cells, it becomes possible to produce part or the whole of the protein or a protein equivalent thereto, which is biologically active, in a stable manner and in large quantities. This has so far been difficult to attain.

The present invention is now illustrated in greater detail with reference to the following Examples. However, it is not intended that the present invention be limited to these Examples.

EXAMPLE 1

(Purification of the Protein Using an MKN45 Cell Culture Supernatant)

MKN45 cells (Naito et al., Gan to Kagaku-ryoho (Cancer and Chemotherapy), 5, 89 (1978)) (obtained from Meneki Seibutsu Kenkyusho) were seeded into eRDF medium containing 5% FBS (fetal bovine serum) as placed in a roller bottle 850 and allowed to multiplicate until a confluent state was attained. Then, the FBS-containing culture supernatants were removed and the cells were washed with two portions of serum-free eRDF medium. After removing the washing medium, 500 ml of serum-free eRDF medium was added and incubation was carried out at 37° C. for 3 to 6 days. After incubation, the culture supernatants were recovered, 500 ml of fresh serum-free eRDF medium was added, and incubation was again conducted. This procedure was repeated several times. The culture supernatants thus recovered were combined and concentrated about 20-fold using a YM30 ultrafiltration membrane (Amicon).

This concentrate was submitted to a heparin-Sepharose column (equilibrated with PBS) and the non-adsorbed fraction was recovered. This fraction was submitted to a ConA-Sepharose column (equilibrated with PBS) and separated into the non-adsorbed fraction and an adsorbed fraction eluted with a PBS solution containing 200 mM α-methyl-D-mannoside. The ConA adsorbed fraction was concentrated using YM30, followed by buffer substitution to 10 mM phosphate buffer (pH 6.8) containing 1 M ammonium sulfate. The new solution was subjected to HPLC using Phenyl-5PW (Tosoh Corp.; equilibrated with 10 mM phosphate buffer (pH 6.8) containing 1 M ammonium sulfate), followed by linear concentration gradient elution with 1 M ammonium sulfate to 0 M ammonium sulfate. A fraction containing the desired protease inhibitor activity was thus recovered.

The fraction was dialyzed against 20 mM Tris-hydrochloride buffer (pH 8) containing 0.05% CHAPS and then subjected to HPLC using DEAE (equilibrated with 20 mM Tris-hydrochloride buffer (pH 8) containing 0.05% CHAPS), followed by linear concentration gradient elution with 0 M to 500 mM NaCl, whereby a fraction showing the desired protease inhibitor activity was recovered. The fraction was dialyzed against 5 mM phosphate buffer (pH 6.8) containing 0.05% CHAPS and then subjected to HPLC using a HCA A-4007 column (product of Mitsui Toatsu Chemicals) (equilibrated with 5 mM phosphate buffer (pH 6.8) containing 0.05% CHAPS), and the non-adsorbed fraction was recovered. The fraction was submitted to GS-520 (equilibrated with PBS containing 0.05% CHAPS) and an active fraction (fraction of about 50 to 30 kDa) was recovered. For eliminating minor bands, the fraction was applied to a YMC pack C4 column (obtained from YMC), linear concentration gradient elution was carried out over 30 minutes using acetonitrile-isopropyl alcohol (3/7) containing 0.1% TFA and varying the concentration thereof from 10% to 50%, and the active fraction was neutralized with 1 M Tris-hydrochloride buffer (pH 8) and then dried under reduced pressure. After drying, the solid obtained was dissolved in PBS containing 0.05% CHAPS to give a purified protein solution.

EXAMPLE 2

(Amino-terminal Amino Acid Sequence and Partial Amino Acid Sequence Determination of the Protein)

The protein having protease inhibitor activity as purified as in Example 1 and eluted by reversed phase HPLC was dried under reduced pressure without neutralization. This was dissolved in 60 μl of 50% TFA (trifluoroacetic acid), added to a polybrene-treated glass filter and subjected to Edman degradation on an Applied Biosystems model 470A sequencer, and the amino acid sequence of an N-terminal region was determined. Phenylhydantoin (PTH)-amino acids were identified using a Mitsubishi Chemical's MCI gel ODS IHU column (0.46×15 cm) and conducting single solvent elution with acetate buffer (10 mM acetate buffer (pH 4.7), 0.01% SDS, 38% acetonitrile) at a flow rate of 1.2 ml/minute and a temperature of 43° C. PTH-amino acids were detected based on the absorbance at 269 nm.

As a result, the N-terminal amino acid sequence shown below in Table 1 was identified.

Then, the same protein having protease inhibitor activity as purified as in Example 1 and eluted by reversed phase HPLC was dissolved in 100 μl of 50 mM Tris-hydrochloride buffer (pH 9.0) containing 4 M urea, lysyl endopeptidase (Achromobacter protease I) was added to the solution, and the reaction was carried out at 37° C. for 8 hours. The resulting peptide mixture was separated by reversed phase HPLC using a YMC pack C8 column (YMC) to give respective peptide fragments. Six peptides were subjected to amino acid analysis using a gaseous phase sequencer (Applied Biosystems model 1470A). The sequences shown in Table 1 were found.

Table 1
Amino Acid Sequences of Peptides
N-terminal: Gly-Pro-Pro-Pro-Ala-Pro-Pro-Gly-Leu-Pro-Ala-Gly-Ala-Asp-Cys-Leu-Asn-Ser-Phe-Thr-Ala-Gly-Val-Pro-Gly-Phe-Val- Leu-Asp-Thr-Xaa-Ala-Ser-Val-Ser-Asn-Gly-Ala-Thr-Phe (SEQ ID NO:1 in the sequence listing)
Partial Amino Acid Sequences
1: Val-Gln-Pro-Gln-Glu-Pro-Leu-Val-Leu-Lys (SEQ ID NO:2 in the sequence listing)
2: Asp-Val-Glu-Asn-Thr-Asp-Trp-Arg-Leu-Leu-Arg-Gly-Asp-Thr-Asp-Val-Arg-Val-Glu-Arg-Lys (SEQ ID NO: 3 in the sequence listing)
3: Ala-Trp-Ala-Gly-Ile-Asp-Leu-Lys (SEQ ID NO:4 in the sequence listing)
4: Ser-Xaa-Val-Tyr-Gly-Gly-Xaa-Leu-Gly-Asn-Lys (SEQ ID NO:5 in the sequence listing)
5: Asp-Pro-Asn-Gln-Val-Glu-Leu-Trp-Gly-Leu-Lys (SEQ ID NO:6 in the sequence listing)
6: Asn-Asn-Tyr-Leu-Arg-Xaa-Xaa-Xaa-Xaa-Ile-Leu-Ala-Xaa-Arg-Gly-Val-Gln (SEQ ID NO:7 in the sequence listing)
(Xaa: amino acid residue not yet identified)

EXAMPLE 3

(Purification of the Protein Using an A549 Cell Culture Supernatant and Amino Acid Sequence Analysis)

A culture supernatant was prepared by cultivating A549 cells (obtained from the Japanese Cancer Research Resources Bank) in the same manner as in Example 1. Using the culture supernatant and proceeding in the same manner as in Example 1, a protein having the inhibitory activity on the protease activity of HGF activator was obtained. Upon SDS-PAGE, this protein showed the same molecular weight as that derived from MKN45 cells. When subjected to the same N-terminal amino acid sequence determination as in Example 1, this protein gave the same sequence as that of the MKN45 cell-derived protein. This suggested the possibility of the protein being identical with the MKN45-derived protein.

EXAMPLE 4

(Method of Assaying the Activity of the Protein Inhibiting the Protease Activity of HGF Activator as Well as the Activity)

One to ten μl of the sample to be assayed was added to 30 to 40 μl of PBS-0.05% CHAPS solution containing 2 to 5 ng of serum-derived HGF activator. After 30 minutes of incubation at 37° C., 5 to 10 μg of single chain HGF was added and incubation was further continued for 2 hours. This incubation mixture was subjected to SDS-polyacrylamide gel electrophoresis under reducing conditions. After electrophoresis, Coomassie Brilliant Blue R250 (CBB)

staining was performed and the proportions of single chain HGF and double chain HGF were compared for activity detection.

The purified protein (10 ng) and 5 ng of serum-derived HGF activator were incubated in 30 to 40 μl of PBS-0.05% CHAPS solution at 37° C. for 30 minutes, then 10 μg of single chain HGF was added, and incubation was further continued for 2 hours. The incubation mixture was subjected to SDS-polyacrylamide gel electrophoresis under reducing conditions followed by staining with CBB. The results are shown in FIG. 1. In the figure, the numeral 1 indicates the case where neither of HGF activator and the protein was added, 2 indicates the case where HGF activator was added but the protein was not added, and 3 indicates the case where HGF activator and the protein were added. Addition of the protein resulted in suppression of the activity of HGF activator converting single chain HGF to double chain HGF.

EXAMPLE 5
(SDS-polyacrylamide Gel Electrophoresis)

For determining the apparent molecular weight of the protein having protease inhibitor activity as purified from the MKN45 cell culture supernatant or A549 cell culture supernatant in Example 1 or Example 2, the protein was subjected to SDS-polyacrylamide gel electrophoresis. The protein finally purified was subjected to SDS-polyacrylamide gel electrophoresis using 12.5% polyacrylamide slab gels, which was conducted under nonreducing conditions. The molecular weight markers used were Molecular weight markers "Daiichi" III for Laemmli method (Daiichi Pure Chemicals). After electrophoresis, color development was performed using a silver stain reagent (Kanto Chemical). Upon relative comparison in migration distance between the protein and the molecular weight markers, the protein obtained from the MKN45 cell culture supernatant or A549 cell culture supernatant showed several fragments or a smear band, presumably due to differences in sugar chain, amino acid residue modification or terminal region, at positions around an apparent molecular weight of about 40,000 daltons as determined by SDS-polyacrylamide gel electrophoresis.

EXAMPLE 6
(Cloning of a Gene Coding for the Protein and Base Sequence Determination)

Two oligonucleotide primers (primer 1 and primer 2) were prepared which were estimable from the sequences Gly-Ala-Asp-Cys-Leu-Asn and Gly-Phe-Val-Leu-Asp-Thr contained in the N-terminal amino acid sequence (SEQ ID NO:1 in the sequence listing) of the protein obtained in Example 2. Two further oligonucleotide primers (primer 3 and primer 4) were synthesized which were estimable from the sequences Ser-Phe-Val-Tyr-Gly-Gly (SEQ ID NO:5) and Gln-Val-Glu-Leu-Trp-Gly (SEQ ID NO:6) in the partial amino acid sequence (Sequence listing 1) of the protein.

The sequences of these primers are shown below:

Primer 1: mixture of 5'-GGNGCNGAYTGYTTRAA-3' (SEQ ID NO:9 in the sequence listing) and 5'-GGNGCNGAYTGYCTNAA-3' (SEQ ID NO:10 in the sequence listing);

Primer 2: mixture of 5'-GTRTCYAANACRAANCC-3' (SEQ ID NO:11 in the sequence listing) and 5'-GTRTCNAGNACRAANCC-31 (SEQ ID NO:12 in the sequence listing);

Primer 3: mixture of 5'-CCNCCRTANACRAANGA-3' (SEQ ID NO:13 in the sequence listing) and 5'-CCNCCRTANACRAARCT-3' (SEQ ID NO:14 in the sequence listing);

Primer 4: mixture of 5'-CCCCANAGYTCNACYTG-3' (SEQ ID NO:15 in the sequence listing) and 5'-CCCCAYAAYTCNACYTG-3' (SEQ ID NO:17 in the sequence listing).

(In the above sequences, N indicates A, G, C or T, Y indicates C or T, and R indicates A or G.)

Separately, total RNA was prepared from MKN45 cells (a stomach cancer cell line) by the method described in Anal. Biochem., 162, 156 (1987) and applied to an oligo(dT) column, whereby poly(A)+RNA was prepared.

Then, an attempt was made to obtain a cDNA fragment corresponding to the N-terminal amino acid sequence of the protein. Using, as the template, the poly(A)+RNA prepared from MKN45 cells and using the two oligonucleotide primers (primer 1 and primer 2) prepared as mentioned above, RT-PCR (reverse transcription-polymerase chain reaction; cf. K. Hayashi (ed.): "PCR Ho no Saishin Gijutu (State-of-art Techniques of PCR)", page 44 and page 52, published Feb. 5, 1995 by Yohdosha) was carried out. The reaction mixture obtained by this RT-PCR was analyzed by polyacrylamide gel electrophoresis, whereupon a DNA fragment of about 56 bp was detected. Therefore, this DNA fragment was extracted from the polyacrylamide gel, followed by phenol-chloroform extraction and ethanol precipitation, whereby the DNA fragment was recovered. The base sequence of the DNA fragment was determined by the dideoxy method.

Then, a primer comprising part of this base sequence, 5'-AACAGCTTTACCG-3' (primer 5) (SEQ ID NO:16 in the sequence listing), was synthesized and used for obtaining the cDNA, as follows.

PCR was carried out using the poly(A)+RNA (as template) prepared previously from MKN45 cells and the primer 3 and primer 5. Further, using the thus-obtained PCR-amplified DNA, the primer 4 and the primer 5, PCR was conducted. As a result, a 480 bp DNA fragment specific to the protein was obtained. The thus-obtained 480 bp DNA fragment was labeled with $^{32}P$ by the method described in "Molecular Cloning" (Cold Spring Harbor Laboratory, 1982) and used as a screening probe.

A human placenta cDNA library (Clonetec) was used as a library for obtaining the full-length cDNA for the protein. First, Escherichia coli Y-1090 was infected with a phage prepared in the form of a human placenta cDNA library (λgt11, Clonetec) to give about 4×10⁵ plaques and incubation in NZY medium was performed overnight at 42° C. Then, the plaques were transferred to a Gene Screening Plus membrane (du Pont). The membrane was placed on a filter paper impregnated with 0.1 M sodium hydroxide-0.5 M Tris hydrochloride buffer (pH 7.5) and allowed to stand for 2 minutes and then placed on a filter paper impregnated with 1.5 M sodium chloride-0.5 M Tris hydrochloride buffer (pH 7.5) and allowed to stand for 5 minutes. After two more repetitions of this series of treatments, the membrane was washed with 2×SSC (two-fold concentrated SSC) and air-dried on a dry filter paper. This membrane was irradiated with UV light at a dose of 20 mJ/cm² for fixation of the DNAs transferred to the membrane. The thus-treated membrane was immersed in 50 ml of a solution comprising 50 mM Tris hydrochloride buffer (pH 7.5), 1 M sodium chloride and 1% SDS and maintained in that state at 65° C. for 2 hours.

Then, the membrane was immersed in 40 ml of a solution comprising 5 ng/ml of the above-mentioned $^{32}P$-labeled probe, 100 μg/ml of salmon sperm, 50 mM Tris hydrochloride buffer (pH 7.5), 1 M sodium chloride and 1% SDS and maintained in that state at 65° C. for 16 hours. Thereafter, this membrane was washed with 2×SSC at room temperature over 5 minutes and then with two portions of 0.1×SSC at room temperature over 30 minutes, and subjected to autoradiography, which gave 84 positive clones supposedly containing cDNA for the protein.

The phage was extracted from each clone with 500 µl of SM buffer (50 mM Tris hydrochloride buffer (pH 7.5), 100 mM sodium chloride, 10 mM magnesium sulfate and 0.01% gelatin) and 20 µl of chloroform. A 100-µl portion of the phage extract and Escherichia coli Y-1090 cells suspended in 100 µl of 10 mM magnesium sulfate were mixed together, and the mixture was sown, together with 3 ml of top agar medium, onto LB agar medium (9 cm) and incubated overnight at 37° C. After confirmation of plaque formation, 3 ml of SM buffer and several drops of chloroform were added and the whole was allowed to stand at room temperature for 1 hour. This phage-containing SM buffer was recovered and centrifuged at 8,000 rpm for 10 minutes, and the supernatant was recovered. A 10-µl portion of the thus-obtained phage solution and 300 µl of an Escherichia coli Y-1090 cell suspension were mixed together, 10 mL of LB medium containing 10 mM magnesium sulfate was added, and shake culture was conducted at 37° C. After bacteriolysis, several drops of chloroform was added, and the mixture was further shaken for 10 minutes and centrifuged at 10,000 rpm for 5 minutes. The supernatant was recovered, DNase I (final concentration 5 µg/ml) and RNase (final concentration 2 µg/ml) were added, and the mixture was allowed to stand at 37° C. for 30 minutes. Then, 5 g of sodium chloride and 1.1 g of PEG 6000 were added, the mixture was allowed to stand at 4° C. for 1 hour and then centrifuged at 10,000 rpm for 15 minutes, and the precipitate was recovered. This precipitate was suspended in 400 µl of SM buffer. The suspension was further subjected to phenol-chloroform treatment and ethanol precipitation, and a phage DNA containing cDNA for the protein was recovered. This DNA was cleaved with the restriction enzyme EcoRI and the cDNA fragments were analyzed by agarose gel electrophoresis. The longest cDNA fragment band in this agarose gel electrophoresis was separated and extracted, and the cDNA fragment was inserted into the plasmid vector pUC19 at its EcoRI site. A plasmid vector, pHAI, containing cDNA for the protein was thus constructed. The base sequence of the cDNA insert in the thus-obtained plasmid vector pHAI was analyzed and the base sequence of the whole gene coding for the protein was determined (SEQ ID NO:8 in the sequence listing).

EXAMPLE 7
(Preparation of an Expression Plasmid for the Protein)

Figure 2:
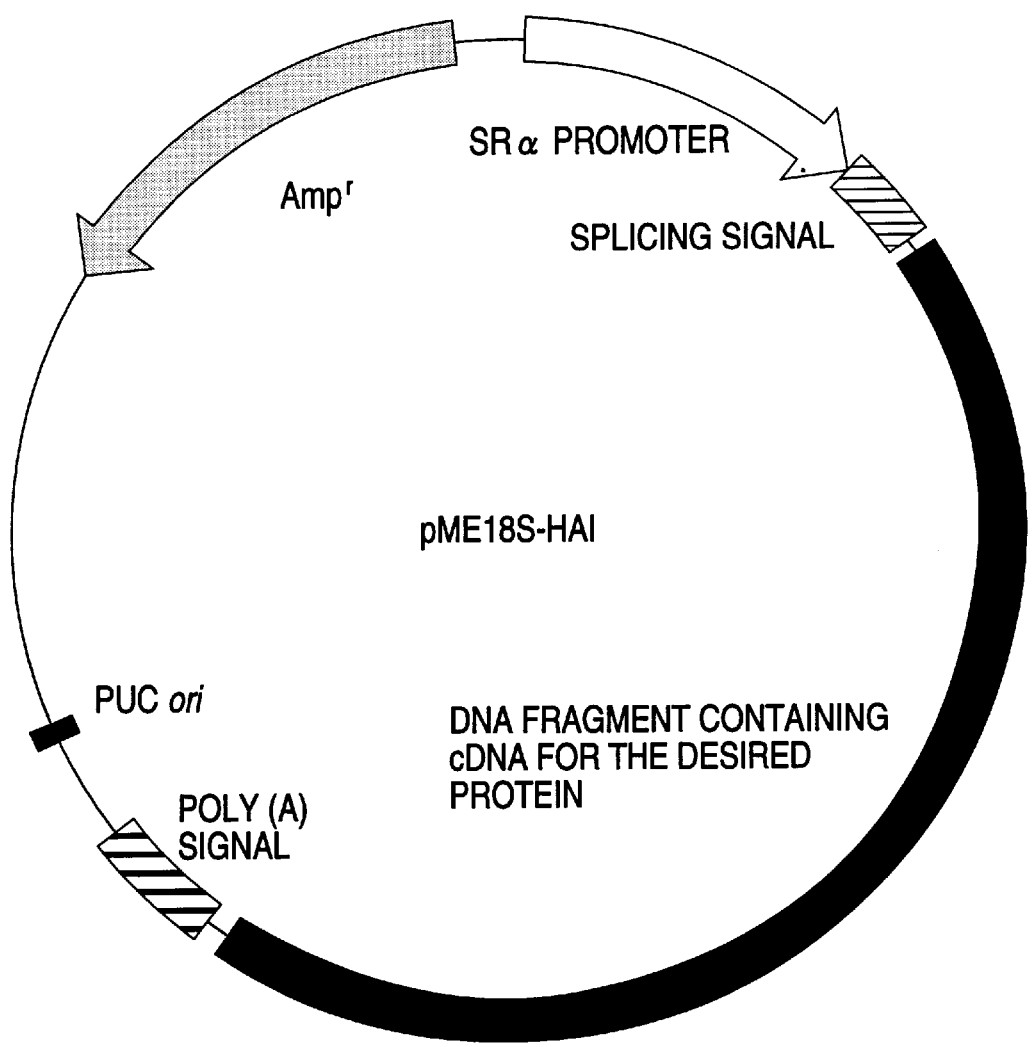
FIG. 2 shows the structure of the plasmid pME18S-HAI.

By treating the plasmid (pHAI) containing cDNA for the protein as obtained in Example 6 with the restriction enzyme EcoRI, it is possible to separate the full-length cDNA fragment coding for the protein (full-length cDNA fragment for the protein, including the translation initiation codon base sequence ATG and the termination codon TGA) from the plasmid vector pUC19. Thus, agarose gel electrophoresis was carried out by the method of Maniatis et al. ("Molecular Cloning", Cold Spring Harbor Laboratory, page 164 (1982)), and an about 2.4 kb EcoRI-EcoRI DNA fragment containing the cDNA for the protein was separated and extracted. The thus-obtained DNA fragment was rendered blunt-ended by the conventional method using T4 DNA polymerase and, then, the DNA fragment was purified by phenol-chloroform extraction and ethanol precipitation and dissolved in 10 µl of water. Separately, 0.05 µg of the expression vector pME18S (Medical Immunology, 20, 27 (1990)) was cleaved in advance with the restriction enzyme XhoI, and the DNA fragment obtained was rendered blunt-ended by the conventional method using T4 DNA polymerase and then purified by phenol-chloroform extraction and ethanol precipitation. This was dissolved in 400 µl of a 1 MM $MgCl_2$ solution in 50 mM Tris-HCl (pH 8), 1 unit of bacterial alkaline phosphatase (Toyobo, BAP-101) was added, and dephosphorylation treatment was conducted at 65° C. for 30 minutes. Then, the DNA fragment was purified from this reaction mixture by phenol-chloroform extraction and ethanol precipitation and dissolved in 10 µl of water. Ligation reaction was carried out in 20 µl of a reaction mixture (66 mM Tris-HCl, pH 7.6, 6.6 mM $MgCl_2$, 10 mM dithiothreitol, 66 AM ATP) containing 0.01 µg of the pME18S vector-derived DNA fragment prepared as mentioned above and 0.1 µg of the above-mentioned blunt-ended EcoRI fragment of cDNA for the protein in the presence of T4 DNA ligase (Toyobo LGA-101) at 14° C. for 12 hours. A 10-µl portion of this T4 DNA ligase reaction mixture was used to transform Escherichia coli HB101 (Takara Shuzo) according to the manual attached thereto. The microorganism was cultured on a medium containing 50 µg/ml of ampicillin and scores of ampicillin-resistant strains were obtained. These transformants were analyzed by the method of Maniatis et al. ("Molecular Cloning", Cold Spring Harbor Laboratory, pages 86–96 (1982)) and, as a result, a plasmid, pME18S-HAI, containing the gene coding for the protein as inserted-at the XhoI restriction enzyme cleavage site occurring between the promoter and polyadenylation site of the expression vector pME18S could be obtained. Its structure is shown in FIG. 2.

EXAMPLE 8
(Obtaining of a Cell Line Expressing the Protein)

The plasmid pME18S-HAI constructed in Example 7 and containing the cDNA for the protein as inserted at the XhoI restriction enzyme cleavage site of the expression vector pME18S was recovered and purified from the recombinant Escherichia coli by the method of Maniatis et al. ("Molecular Cloning", Cold Spring Harbor Laboratory, pages 86–96 (1982)) and thus a large amount of the expression plasmid DNA for the protein was obtained. COS cells were transformed by transfection thereof with the expression plasmid DNA. Thus, COS cells were first cultured in eRDF medium containing 10% FBS (fetal bovine serum) in tissue culture dishes 9 cm in diameter until a semiconfluent condition. Then, the medium was removed from the dishes, and a DNA solution prepared as mentioned below was added dropwise thereto as mentioned below. First, for each dish 9 cm in diameter, a solution was prepared in an Eppendorf centrifuge tube by adding thereto 300 µl of 2×HEBS solution (2×HEBS solution: 1.6% sodium chloride, 0.074% potassium chloride, 0.05% disodium hydrogen phosphate dodecahydrate, 0.2% dextrose, 1% HEPES (pH 7.05)) and 10 µg of the plasmid DNA and making the volume 570 µl with sterilized water. Then, while adding 30 µl of 2.5 M calcium chloride solution to the DNA solution, the tube contents were stirred vigorously using a vortex mixer for several seconds. The resulting mixture was allowed to stand at room temperature for 30 minutes, with occasional stirring at intervals of about 10 minutes using a vortex mixer. The thus-prepared DNA solution was laid on the cells mentioned above and the whole was allowed to stand at room temperature for 30 minutes. Then, 9 ml of eRDF medium (Kyokuto Pharmaceutical) supplemented with 10% FBS was added to each dish and incubation was performed at 37° C. for 4 to 5 hours in the presence of 5% $CO_2$. Then, the medium was removed from each dish and the cells were washed with 5 ml of 1×TBS++ solution (1×TBS++ solution: 25 mM Tris-hydrochloride (pH 7.5), 140 mM sodium chloride, 5 mM potassium chloride, 0.6 mM disodium hydrogen phosphate, 0.08 mM calcium chloride, 0.08 mM magnesium chloride). After removing the 1×TBS++ solution, the cells were covered with 5 ml/dish of 1×HEBS solution containing 10% DMSO (dimethyl sulfoxide) and allowed to stand at room temperature for 1 to 2 minutes. The supernatant was then removed. The cells were again washed with 5 ml of 1×TBS++ solution, 10 ml of eRDF medium supplemented with 10% FBS was added to each dish and incubation was performed at 37° C. in the presence of 5% $CO_2$. After the lapse of 48 hours, the medium was recovered. The supernatant recovered was 20-fold concentrated and assayed for inhibitory activity against HGF activator in the same manner as in Example 4. The inhibitory activity was confirmed.

While the invention has been described in detail and with reference to specific embodiments thereof, it will be apparent to one skilled in the art that various changes and modifications can be made therein without departing from the spirit and scope thereof.

What is claimed is:

1. An isolated DNA molecule encoding a protein that has the following physio-chemical properties:
   (1) has a molecular weight of about 40,000 daltons, as determined by SDS-polyacrylamide gel electrophoresis;
   (2) inhibits hepatocyte growth factor activator protease activity; and
   (3) comprises each of the amino acid sequences set forth in SEQ ID NO:1, SEQ ID NO:2, SEQ ID NO:3, SEQ ID NO:4, SEQ ID NO:5, SEQ ID NO:6, and SEQ ID NO:7.

2. An isolated DNA molecule encoding a protein comprising the amino acid sequence set forth in SEQ ID NO:18.

3. An isolated DNA molecule encoding a protein comprising the amino acid sequence from amino acid 36 (glycine) to amino acid 513 (leucine) set forth in SEQ ID NO:18.

4. The isolated DNA molecule of claim 2, wherein said DNA molecule comprises the nucleotide sequence set forth in SEQ ID NO:8.

5. The isolated DNA molecule of claim 3, wherein said DNA molecule comprises the nucleotide sequence from the $106^{th}$ nucleotide (guanine) to the $1542^{nd}$ nucleotide (adenine) set forth in SEQ ID NO:8.

6. An expression vector comprising the isolated DNA molecule of claims 1, 2, 3, 4 or 5.

7. A transformant obtained by transformation of a host cell with the expression vector of claim 6.

8. The transformant of claim 7, wherein said host cell is an animal cell.

9. A method for producing a protein which inhibits hepatocyte growth factor activator protease activity comprising culturing the transformant of claim 7, and recovering said protein from said culture to thereby produce said protein.

10. The method or claim 9, wherein said host cell is an animal cell.

* * * * *